United States Patent
Hentz et al.

(10) Patent No.: US 10,119,856 B2
(45) Date of Patent: Nov. 6, 2018

(54) METHOD FOR DETECTING A PERTURBATION BY HYSTERETIC CYCLE USING A NONLINEAR ELECTROMECHANICAL RESONATOR AND DEVICE USING THE METHOD

(71) Applicants: COMMISSARIAT A L'ENERGIE ATOMIQUE ET AUX ENERGIES ALTERNATIVES, Paris (FR); ECOLE NATIONALE TRAVAUX PUBLICS DE L'ETAT, Vaulx-en-Velin (FR); INSTITUT NATIONAL SCIENCES APPLIQUEES DE LYON, Villeurbanne (FR); CENTRE NATIONAL DE LA RECHERCHE SCIENTIFIQUE, Paris (FR)

(72) Inventors: Sebastien Hentz, Varces Allieres et Risset (FR); Sebastien Baguet, Villeurbanne (FR); Regis Dufour, Lyons (FR); Claude-Henri Lamarque, Farnay (FR); Van Nghi Nguyen, Villeurbanne (FR)

(73) Assignees: COMMISSARIAT A L'ENERGIE ATOMIQUE ET AUX ENERGIES ALTERNATIVES, Paris (FR); ECOLE NATIONALE TRAVAUX PUBLICS DE L'ETAT, Vaulx-en-Velin (FR); INSTITUT NATIONAL SCIENCES APPLIQUEES DE LYON, Villeurbanne (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 592 days.

(21) Appl. No.: 14/558,314

(22) Filed: Dec. 2, 2014

(65) Prior Publication Data
US 2015/0153221 A1   Jun. 4, 2015

(30) Foreign Application Priority Data

Dec. 3, 2013   (FR) ..................... 13 61972

(51) Int. Cl.
G01H 13/00   (2006.01)
G01N 29/36   (2006.01)
(Continued)

(52) U.S. Cl.
CPC ......... G01H 13/00 (2013.01); B81C 99/0045 (2013.01); G01H 11/00 (2013.01);
(Continued)

(58) Field of Classification Search
CPC .... G01H 13/00; G01H 11/00; B81C 99/0045; H01J 49/26; H03H 9/02; H03H 9/02259;
(Continued)

(56) References Cited

U.S. PATENT DOCUMENTS 8,653,716 B2   2/2014 Hentz et al.
2011/0221301 A1*  9/2011 Hentz ................ G01C 19/56
                                                310/309
(Continued)

FOREIGN PATENT DOCUMENTS

DE   102005010498 A1   9/2006
EP       2365282 A1   9/2011
(Continued)

OTHER PUBLICATIONS

N. Kacem, et al., "Nonlinear Dynamics of Nanomechanical Beam Resonators: Improving the Performance of NEMS-Based Sensors", Nanotechnology, 2009, pp. 1-11, vol. 20, IOP Publishing.
(Continued)

Primary Examiner — Manish S Shah
Assistant Examiner — Rose M Miller
(74) Attorney, Agent, or Firm — Baker & Hostetler LLP

(57) ABSTRACT

A method is provided for detecting a perturbation with respect to an initial state, of a device including at least one
(Continued)

resonant mechanical element exhibiting a physical parameter sensitive to a perturbation such that the said perturbation modifies the resonance frequency of the said resonant mechanical element. A device is provided for detecting a perturbation by hysteretic cycle having at least one electromechanical resonator with nonlinear behavior and means for actuation and detection of the reception signal via a transducer so as to analyze the response signal implementing the method. A mass sensor and a mass spectrometer using the device are also provided.

8 Claims, 7 Drawing Sheets

(51) Int. Cl.
  *H01J 49/26* (2006.01)
  *H03H 9/02* (2006.01)
  *B81C 99/00* (2010.01)
  *G01H 11/00* (2006.01)
  *H03H 9/24* (2006.01)
  *H03H 7/00* (2006.01)
(52) U.S. Cl.
  CPC .............. *G01N 29/36* (2013.01); *H01J 49/26* (2013.01); *H03H 9/02* (2013.01); *H03H 9/02259* (2013.01); *B81B 2201/0214* (2013.01); *B81B 2201/0271* (2013.01); *B81B 2203/0118* (2013.01); *G01N 2291/014* (2013.01); *H03H 9/2457* (2013.01); *H03H 2007/006* (2013.01); *H03H 2009/02267* (2013.01)
(58) Field of Classification Search
  CPC .............. H03H 9/02244; H03H 9/2457; H03H 2007/006; H03H 2009/02267; B81B 2201/0214; B81B 2201/0271; B81B 2201/0285; B81B 2203/0118; G01N 29/36; G01N 29/022; G01N 29/036; G01N 29/42; G01N 2291/014; G01N 2291/02408; G01N 2291/02416; G01N 2291/0255; G01N 2291/0256; G01N 2291/0257
  USPC .. 73/579, 24.03, 24.06, 61.71, 61.72, 61.75, 73/61.79, 64.53
  See application file for complete search history.

(56) References Cited

U.S. PATENT DOCUMENTS

| | | | |
|---|---|---|---|
| 2012/0206594 A1* | 8/2012 | Datskos | G01N 29/022 348/135 |
| 2013/0047710 A1* | 2/2013 | Rhoads | G01N 29/022 73/64.53 |
| 2013/0154440 A1 | 6/2013 | Hentz | |

FOREIGN PATENT DOCUMENTS

| | | |
|---|---|---|
| WO | 02093111 A1 | 11/2002 |
| WO | 2010139055 A1 | 12/2010 |
| WO | 2012034949 A1 | 3/2012 |

OTHER PUBLICATIONS

Ville Kaajakari, et al., "Phase Noise in Capacitatively Couled Micromechanical Oscillators", IEEE Transactions on Ultrasonics, Ferroelectrics, and Frequency Control, Dec. 2005, pp. 2322-2331, vol. 52, No. 12, IEEE.

Wenhua Zhang, et al., "Application of Parametric Resonance Amplification in a Single-Crystal Silicon Micro-Oscillator Based Mass Sensor", Sensors and Actuators A: Physical, Jul. 2005, pp. 23-30, vol. 122, No. 1, Elsevier B.V.

Mohammad I. Younis, et al., "Exploration of New Concepts for Mass Detection in Electrostatically-Actuated Structures Based on Nonlinear Phenomena", Journal of Computational and Nonlinear Dynamics, Apr. 2009, pp. 021010-1 thru 021010-15, vol. 4, No. 2, ASME.

Vijay Kumar, et al., "Modeling, Analysis, and Experimental Validation of a Bifurcation-Based Microsensor", Journal of Microelectromechanical Systems, Jun. 2012, pp. 549-558, vol. 21, No. 3, IEEE Service Center, USA, XP011445756.

J. Chaste, et al., "A Mechanical Mass Sensor with Yoctogram Resolution", Nature Nanotechnology, 2012, pp. 1-19.

Vincent Gouttenoire, et al., "Digital and FM Demodulation of a Doubly Clamped Single-Walled Carbon Nanotube Oscillator: Towards a Nanotube Cell Phone", Small, 2010, pp. 1060-1165, vol. 6, No. 9, Wiley-VCH Verlag GmbH.

E Mile, et al., "In-Plane Nanoelectromechanical Resonators Based on Silicon Nanowire Piezoresistive Detection", Nanotechnology, Apr. 2010, pp. 1-7, No. 21, No. 16, IOP Publishing.

* cited by examiner

METHOD FOR DETECTING A PERTURBATION BY HYSTERETIC CYCLE USING A NONLINEAR ELECTROMECHANICAL RESONATOR AND DEVICE USING THE METHOD

CROSS-REFERENCE TO RELATED APPLICATION

This application claims priority to foreign French patent application No. FR 1361972, filed on Dec. 3, 2013, the disclosure of which is incorporated by reference in its entirety.

FIELD OF THE INVENTION

The field of the invention is that of microsystems, dubbed MEMS for MicroElectroMechanical Systems and more precisely that of MEMS resonators, exhibiting a movable part that may be subjected to vibrations, for applications such as inertial sensors, pressure sensors, gas or mass sensors. By extension, it is possible to speak of MEMS/NEMS devices for devices that may exhibit some of their dimensions smaller than a micron, or indeed of the order of a nanometre.

BACKGROUND

Generally, a resonant sensor is characterized by a resonance frequency which depends mainly on the mass of the movable part of the sensor, the geometric parameters of the mechanical parts of the sensor and the physical parameters of the materials forming the various parts of the sensor, as well as the quality factor dependent on the energy losses of the resonant sensor. The dependency of the resonance frequency with the aforementioned physical parameters, thereby makes it possible to carry out a measurement of an exterior perturbation of one of these parameters (for example a variation of mass, an acceleration, a pressure, etc.).

Thus in applications of this type, a resonant mechanical element, that may for example be a clamped/clamped or clamped free nano-beam, is conventionally equipped with at least one electrode for actuation $E_A$ making it possible to apply a drive voltage, such as illustrated in FIG. 1 and which represents a clamped beam P.

The electrostatic loading generated by the drive voltage may then be written $$F_{act} = \frac{1}{2} \varepsilon_0 S \frac{V^2}{(g-x)^2}$$

where S is the facing surface area, g the gap between the drive electrode and the beam, V the actuation voltage comprising a DC component and an AC component such that: $V = V_{dc} + V_{ac} \cdot \cos \Omega t$. The DC voltage $V_{dc}$ bends the beam statically whereas the harmonic voltage $V_{ac} \cdot \cos \Omega t$ bends it dynamically.

Conventionally the resonator is caused to vibrate at its fundamental bending frequency so as to obtain the maximum of amplitude. By virtue of an inverse electrical transduction, it is then possible to determine the resonance frequency of the device from reading the signal.

In the case for example of a mass sensor that may be the one shown diagrammatically in FIG. 1, under the effect of an added mass or of an axial load, the resonance frequency is shifted from the frequency $f_0$, to the frequency $f_{res}$, as illustrated in FIG. 2. The measurement of the frequency shift $\delta f$ is equal to $f_0 - f_{res}$ with a resonance frequency measured $f_{res}$, after detection that may be of capacitive type.

In a conventional manner, the amplitude of actuation of the resonator is maintained below a so-called critical amplitude, beyond which the vibration regime becomes nonlinear.

Nonetheless, to improve the performance of a resonator, it is possible to seek to obtain the largest possible amplitude of actuation of the resonator. The amplitude then exceeds a threshold value corresponding to the critical amplitude beyond which the vibration regime becomes non-linear, causing the occurrence of hysteresis phenomena. The occurrence of this non-linear regime is notably described in the article by N. Kacem, S. Hentz, D. Pinto, B. Reig, and V. Nguyen, "Nonlinear dynamics of nanomechanical beam resonators: improving the performance of NEMS-based sensors," *Nanotechnology*, vol. 20, p. 275501, 2009 or in patent application EP 2 365 282.

FIG. 3 illustrates this principle, within the framework of the frequency response of a nano-resonator of beam type with a so-called softening non-linear device (the peak is deviated towards the low frequencies). The principle would be identical with a perfectly linear or non-linear response of a so-called stiffening device (peak deviated towards the right). In the absence, for example, of any additional mass to be detected, the response of the nano-resonator as a function of frequency for amplitude values beyond the linearity threshold has the behaviour of the initial response curve $F_0$.

Under the effect of a very meagre added mass, the response curve of the nano-resonator is shifted towards the low frequencies to give the curve $F_M$. Conventional frequency measurements consist in detecting this shift $\Delta\Omega$ and in measuring it. However, this shift becomes very small and difficult to distinguish from measurement noise for very small masses.

It is theoretically possible to improve the frequency sensitivity by decreasing the sizes and/or by increasing the signal-to-noise ratio, that is to say by actuating the resonators in a more significant manner. However, under these conditions, the nano-resonators have a very strongly non-linear behaviour, a source of instabilities and of mixing of low and high frequency noise that are liable to degrade the reliability and precision of the measurements by frequency shifting as described in the article by V. Kaajakari, J. K. Koskinen, and T. Mattila, "Phase noise in capacitively coupled micromechanical oscillators," *IEEE transactions on ultrasonics ferroelectrics, and frequency drive*, vol. 52, no. 12, pp. 2322-31, December 2005.

Another route for improving the sensitivity of resonant sensors consists in defining alternative detection principles based on the exploitation of non-linear phenomena. Several studies have already been described in the literature, which seek for example to amplify the resonator's response amplitude by means of internal or parametric resonances and notably in the articles by: W. Zhang and K. L. Turner, "Application of parametric resonance amplification in a single-crystal silicon micro-oscillator based mass sensor," *Sensors and Actuators A: Physical*, vol. 122, no. 1, pp. 23-30, July 2005 or by M. I. Younis and F. Alsaleem, "Exploration of New Concepts for Structures Based on Nonlinear Phenomena," *Journal Of Computational And Nonlinear Dynamics*, vol. 4(2), 021010, 2009. But these resonances exist only when the resonators have very particular geometries and excitations.

An alternative also disclosed within the field consists in using the jumps in amplitude in the neighbourhood of singular operating points and is illustrated by virtue of FIG. 4. More precisely, this entails causing the resonator to vibrate without extra mass at a fixed frequency $\Omega_{op}$ slightly lower than that of the limit point $A_{lim}$ of the response curve $F_0$ (without perturbation). More precisely, this point $A_{lim}$ corresponds to a bifurcation point, corresponding to a change of increase and of decrease of the frequency.

The trend of this response curve is characteristic of a non-linear behaviour and, at the chosen excitation frequency $\Omega_{op}$, it possesses two stable operating points $A_1$ and $A_2$.

FIG. 4 thus highlights a so-called unstable frequency band $B_{INS}$ in which two stable amplitudes can correspond to a single frequency: for example the amplitudes A1 and A2 to the frequency $\Omega_{op}$, whereas below a certain frequency value, it is possible to define a so-called stable frequency band $B_S$ in which there is indeed correspondence between a frequency and a single stable amplitude.

In this configuration, when a mass is added to the resonator, the response curve is shifted towards the curve $F_M$. Given that this new response curve with added mass possesses only a single operating point B at the frequency $\Omega_{op}$, an abrupt jump in amplitude from $A_1$ to B occurs, as described in the article by V. Kumar, S. Member, Y. Yang, S. Member, G. T. Chiu, and J. F. Rhoads, "Modeling, Analysis, and Experimental Validation of a Bifurcation-Based Microsensor," Journal of Microelectromechanical Systems, vol. 21, no. 3, pp. 549-558, 2012.

In contradistinction to frequency detection based on $\Delta\Omega$, this jump is all the larger as the extra mass is small, thereby rendering this technique particularly beneficial. Moreover, the detection threshold in terms of mass can be tailored with the value of the frequency $\Omega_{op}$. It is thus possible to quantify the mass deposited by virtue of the amplitude of the jump in amplitude, but also simply to detect the presence or otherwise of the mass, and to count the number of particles which have deposited.

Nonetheless, once mass detection has been effected, the particle-free nano-beam must be able to regain its initial state, that is to say regain the state A1. In the converse case, if instead of dropping back to its operating point A1, the nano-beam jumps from its state B to the state A2, it becomes, in this case, difficult to again detect an appreciable amplitude variation. A reinitialization phase becomes necessary in order to carry out new sensitive measurements.

SUMMARY OF THE INVENTION

In this context and to solve the aforementioned problem, the subject of the present invention is a method for detecting a perturbation by hysteretic cycle comprising at least one electromechanical resonator with nonlinear behaviour and means for actuation and for detection of the reception signal via a transducer so as to analyse the response signal.

More precisely the subject of the present invention is a method for detecting a perturbation with respect to an initial state, of a device comprising at least one resonant mechanical element exhibiting a physical parameter sensitive to a perturbation such that the said perturbation modifies the resonance frequency of the said resonant mechanical element, the said method comprising:

the excitation of the resonant mechanical element making it possible to cause the said resonant mechanical element to vibrate in a domain of non-linear amplitude response at a vibration frequency $\Omega$, the said amplitude and the said frequency being linked by an initial function $f_0$ ($\Omega$), the said perturbation generating a measurement function $f_M$ ($\Omega$);

the detection and the analysis of the variations of amplitude of vibrations of the said mechanical element between an amplitude of the function $f_0$ ($\Omega$) and an amplitude of the function $f_M$ ($\Omega$) resulting from the excitation, characterized in that, the said function $f_0$ ($\Omega$) exhibiting a so-called bifurcation frequency $\Omega_{lim}$, corresponding to a change of increase and of decrease of the frequency as a function of amplitude and possessing at least one unstable frequency band $B_{INS}$ in which there exist at least two stable amplitudes for one and the same frequency, and at least one stable frequency band $B_S$ in which a single stable amplitude corresponds to a single frequency, the excitation step is carried out:

at a variable vibration frequency within a frequency band defined by a minimum frequency $\Omega_{min}$ and a maximum frequency $\Omega_{max}$ and according to at least one frequency cycle centred on a central frequency $\Omega_{op}$, one of the said minimum or maximum frequencies being situated in the stable frequency band of the said initial function, the other maximum or minimum frequency being situated in the unstable frequency band.

According to a variant of the invention, the said vibration frequency varies around a central frequency $\Omega_{op}$ according to the law: $\Omega(t)=\Omega_{op}+\delta\Omega \cos(\epsilon\pi t+\varphi)$ with $\epsilon$ the frequency scan rate, $\varphi$ having a value lying between 0 and $2\pi$.

The vibration frequency can of course vary according to any type of law, such as for example a square law, that can be described in the form of an infinite series:

$$\Omega(t) = \Omega_{op} + \delta\Omega \cdot \frac{4}{\pi} \sum_{n=0}^{\infty} \frac{\sin((2n+1)\epsilon\pi t)}{(2n+1)}.$$

According to a variant of the invention, the maximum frequency $\Omega_{max}$ is such that the factor in absolute value $|\Omega_{lim}-\Omega_{max}|$ lies between $0.\,\Omega_{op}$ and $10^{-1}\cdot\Omega_{op}$ and advantageously between $10^{-9}\cdot\Omega_{op}$ and $10^{-1}\cdot\Omega_{op}$.

According to a variant of the invention, the method comprises a processing step making it possible to temporally adjust the said central frequency $\Omega_{op}$ in such a way that the said central frequency belongs to the frequency band defined by $\Omega_{min}$ and $\Omega_{max}$ with one of the said minimum or maximum frequencies being situated in the stable frequency band of the said initial function, the other maximum or minimum frequency being situated in the unstable frequency band.

According to a variant of the invention, the physical parameter is the mass, the frequencies $\Omega_{min}$ and $\Omega_{max}$ determining the thresholds of the largest mass and of the smallest mass to be detected.

According to a variant of the invention, the frequency scan rate c of a cycle lies between about 1 Hz and 100 kHz or with a ratio $\epsilon\pi/\Omega_{op}$ such that $0<\epsilon\pi/\Omega_{op}<10^{-1}$.

The subject of the invention is also a device for detecting a perturbation with respect to an initial state comprising:

at least one resonant mechanical element exhibiting a physical parameter sensitive to a perturbation such that the said perturbation modifies the resonance frequency of the said resonant mechanical element;

a source of excitation of the resonant mechanical element making it possible to cause the said resonant mechanical element to vibrate in a domain of non-linear amplitude response at a vibration frequency $\Omega$, the said amplitude and the said frequency being linked by an initial function $f_0 (\Omega)$, the said perturbation generating a measurement function $f_M (\Omega)$;

means for detecting and analysing the variations of amplitude of vibrations of the said mechanical element between an amplitude of the function $f_0 (\Omega)$ and an amplitude of the function $f_M (\Omega)$, characterized in that:

the said function $f_0 (\Omega)$ exhibits a so-called bifurcation frequency $\Omega_{lim}$, corresponding to a change of increase and of decrease of the frequency as a function of amplitude and possesses at least one unstable frequency band ($B_{INS}$) in which there exist at least two stable amplitudes for one and the same frequency, and at least one stable frequency band ($B_S$) in which a single stable amplitude corresponds to a single frequency;

the said excitation source comprises means which vary the said vibration frequency in a frequency band defined by a minimum frequency $\Omega_{min}$ and a maximum frequency $\Omega_{max}$ and according to at least one frequency cycle centred on a central frequency $\Omega_{op}$, one of the said minimum or maximum frequencies being situated in the stable frequency band of the said initial function, the other maximum or minimum frequency being situated in the unstable frequency band.

According to a variant of the invention, the said excitation source comprises piezoelectric or thermoelastic or magnetic or electrostatic or optical means.

According to a variant of the invention, the said detection means comprise at least one transducer of piezoresistive or capacitive or piezoelectric or optical or magnetic type.

According to a variant of the invention, the resonant mechanical element is a resonator of beam type, the excitation source comprising an actuation electrode facing the said resonator.

According to a variant of the invention, the resonator is a resonator of beam type of nanometric dimensions, the drive electrode making it possible to apply voltages of the order of a few Volts, the gap between the said drive electrode and the said resonator being of the order of a few hundred nm, and for example between 10 nm and 1 µm.

The subject of the invention is further a mass sensor comprising a device according to the invention.

The subject of the invention is also a gas or particle detector comprising a device according to the invention, allowing the quantification of the concentration of the species present, which get absorbed in a chemical functionalization layer.

The subject of the invention is also a mass spectrometer comprising a device according to the invention making it possible to measure the mass of each of the particles sitting on the said device.

BRIEF DESCRIPTION OF THE DRAWINGS

The invention will be better understood and other advantages will become apparent on reading the nonlimiting description which follows and by virtue of the appended figures among which.

DETAILED DESCRIPTION

According to the present invention, the device comprises at least one resonant mechanical element, also dubbed a resonator, and an excitation source capable of bringing the said resonator into its non-linear operating domain by actuation with an appropriate amplitude, doing so whatever the dimensions and the transduction principle thereof.

This may for example be a device with piezoelectric, thermoelastic, magnetic, electrostatic or else optical actuation, and with piezoresistive, capacitive, piezoelectric, optical or magnetic detection, according to the known art.

Advantageously, the resonator can be a resonator of silicon beam type, of nanometric dimensions, for example a few µm long, a few 100 nm thick and wide, resonating at frequencies of the order of some ten MHz.

Advantageously the resonator can be a resonator whose non-linearity coefficient is able to be controlled so as to render it softening: the curve plotting the resonance frequency dependent amplitude being oriented towards the low frequencies with respect to a straight line perpendicular to the abscissa axis, or stiffening: the curve plotting the resonance frequency dependent amplitude being oriented towards the high frequencies with respect to a straight line perpendicular to the abscissa axis. To do this, it is notably possible to use an electrostatic electrode in proximity as described in the reference of Kacem et al, "Nonlinear dynamics of nanomechanical beam resonators: improving the performance of NEMS-based sensors," *Nanotechnology*, vol. 20, p. 275501, 2009 or in patent application EP 2 365 282, for example with a gap of the order of 100 nm. The voltages used can reach a few Volts, AC or DC.

These are tailored as a function of the device, for example so as to obtain a vibration amplitude between 1 time the critical amplitude and 10 times the latter, as described in the article by N. Kacem, S. Hentz, D. Pinto, B. Reig and V. Nguyen, "Nonlinear dynamics of nanomechanical beam resonators: improving the performance of NEMS-based sensors," Nanotechnology, vol. 20, p. 275501, 2009.

The present invention is described hereinafter within the framework of a perturbation corresponding to a detection of mass, typically of particles, but can be applied more widely to any detection of perturbation engendering a variation of resonance frequency of the vibrating element excited according to the means which are described in the present invention, and which is illustrated hereinafter within the framework of a softening resonator.

Figure 1:
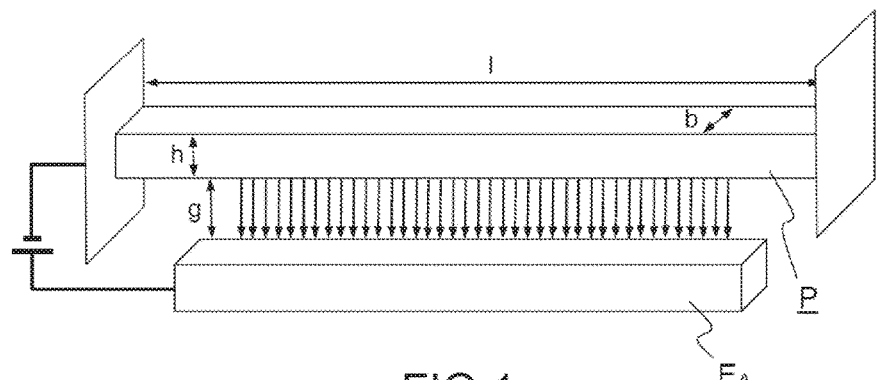
FIG. 1 illustrates an example of setting a vibrating mechanical element into vibration, actuated by a drive electrode according to the known art.
Figure 2:
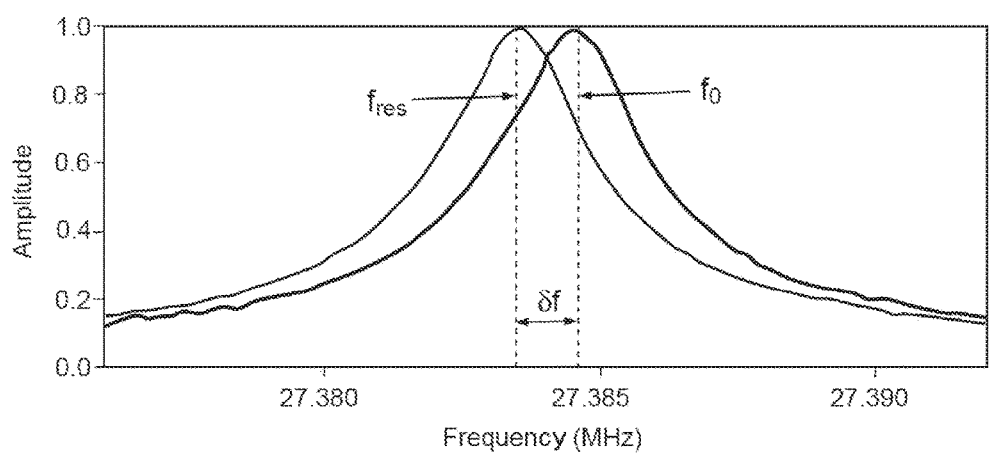
FIG. 2 illustrates the shift in resonance frequency of a vibrating element of the known art, between an initial state and a measurement state after mass variation.
Figure 3:
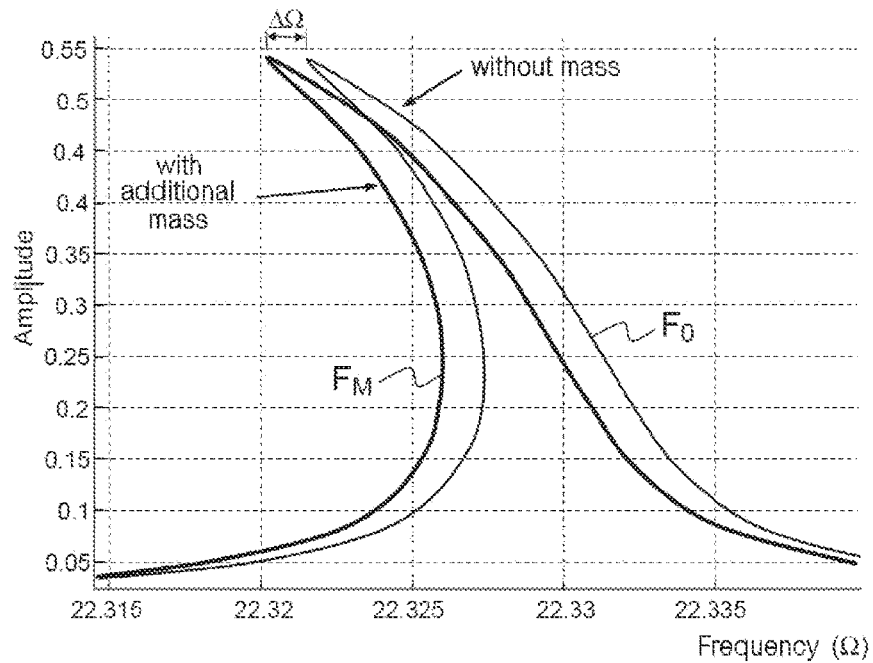
FIG. 3 illustrates the frequency response curve of a vibrating mechanical element, excited in a non-linear and stationary regime.
Figure 4:
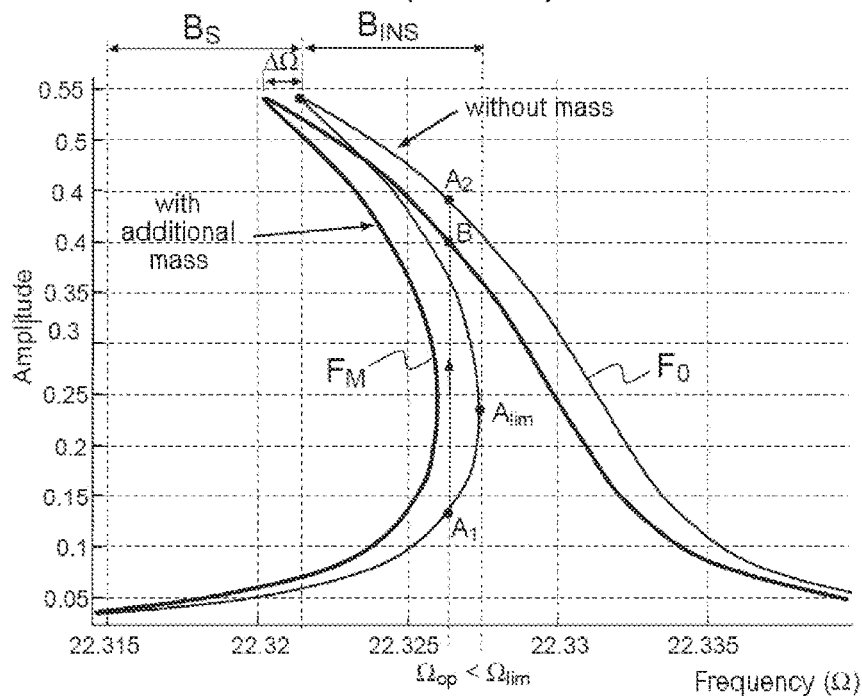
FIG. 4 illustrates the exploitation of the non-linear regime in terms of amplitude variation, between the response curves corresponding to an initial state and to a measurement state after mass variation, within the framework of a so-called softening resonator.

Thus, referring to FIG. 4 explained previously, during a detection of a perturbation, in this instance an additional mass shifting the resonance frequency onto the curve $F_M$, if the response stabilizes in the state B with the added mass, at the start of the latter, the response returns either to the state $A_1$ or to the state $A_2$:

- if this entails the state $A_1$, the following mass variation can be readily detected;
- if on the contrary, the passage takes place from the state B to the state $A_2$, the following added mass to be detected generates a jump of small amplitude, which is difficult to measure precisely.

To alleviate this problem, the present invention proposes a device comprising actuation means integrating a measurement reinitialization phase making it possible not to regain the set position corresponding to the state A2, and allowing or forcing a return to the state A1 in all typical cases.

Figure 5:
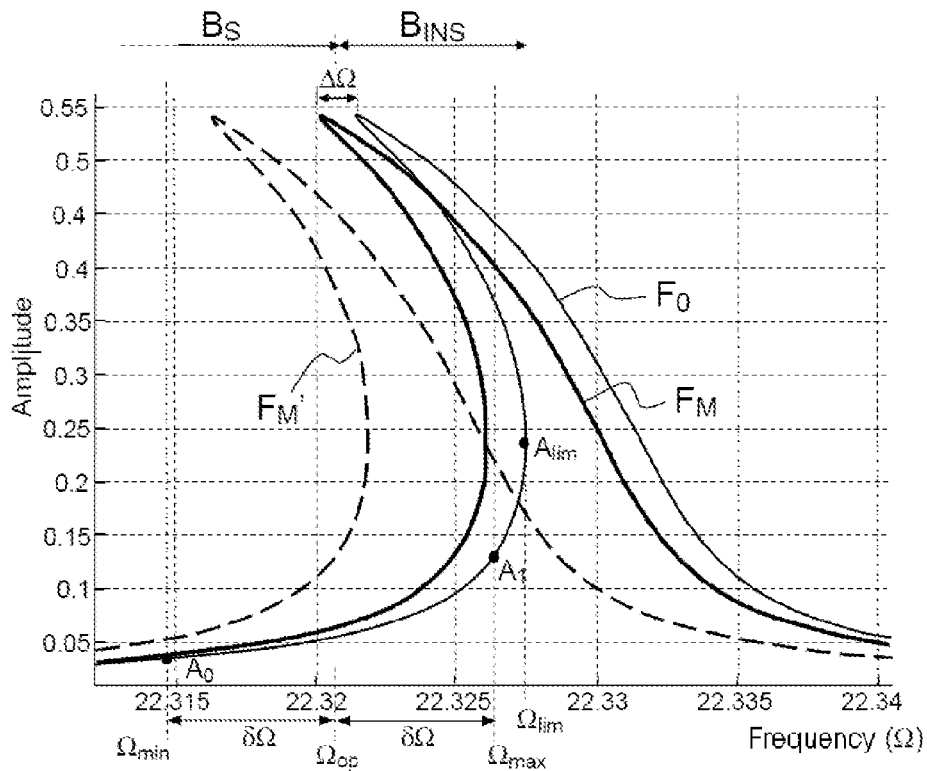
FIG. 5 illustrates the response curves generated by the excitation source used in the device of the invention making it possible to integrate a process for reinitializing the measurement, within the framework of a so-called softening resonator.

The means of actuation of the present invention are such that they make it possible to carry out the frequency scan cycle illustrated in FIG. 5, in so-called "slow" time with respect to the period associated with $\Omega_{op}$ in such a way that $0<\varepsilon\pi/\Omega_{op}<10^{-1}$, doing so in a range of well defined frequencies between a minimum frequency bound $\Omega_{min}$ and a maximum frequency bound $\Omega_{max}$, such that the said maximum frequency belongs to the span of unstable frequencies $B_{INS}$ (two possible stable amplitudes for one and the same frequency), the said minimum frequency belonging to the span of stable frequencies $B_s$ (a single possible amplitude for one and the same frequency), the benefit of the two possible amplitudes respectively lower and higher than the amplitude $A_{lim}$ allowing, as illustrated in FIGS. 4 and 5, the detection of a significant variation in amplitude, the curve $F_M'$ relating to another added mass.

Figure 6A:
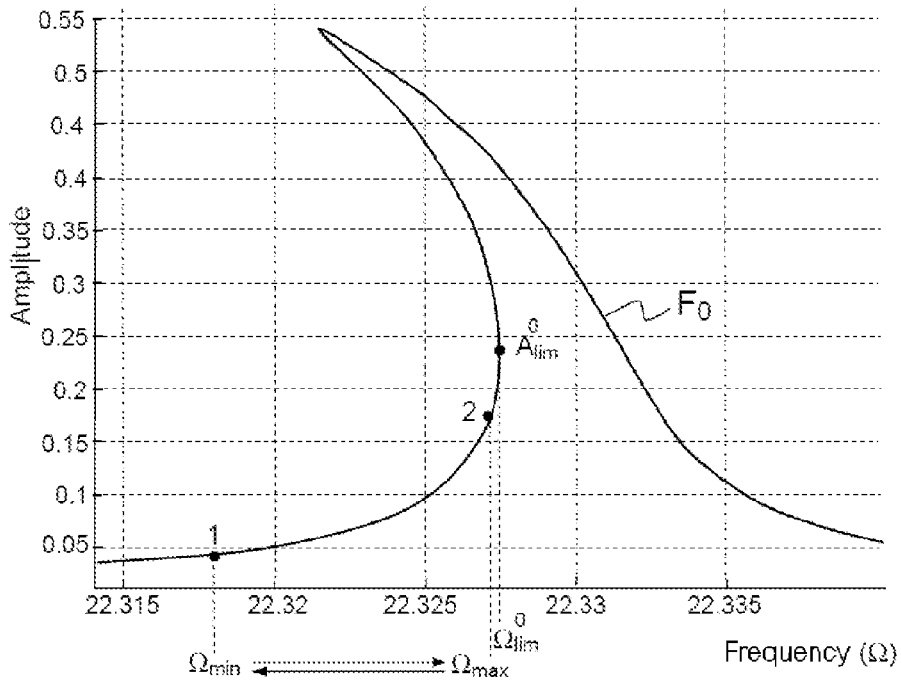
FIGS. 6a, 6b and 6c illustrate the detail of the frequency scan cycles respectively in the absence of particle detection, in the presence of particle detection.

FIG. 6a illustrates more precisely, the cycle followed in the absence of any particle. The curve $F_0$ is traversed between the points 1 and 2, there is no hysteresis cycle nor any associated jump in amplitude.

Figure 6B:
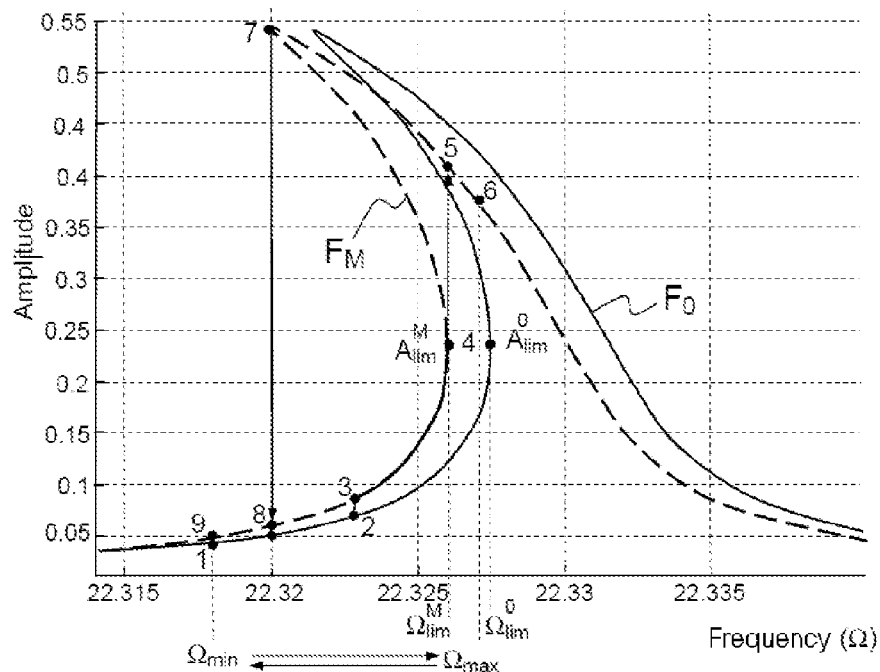
Figure 6C:
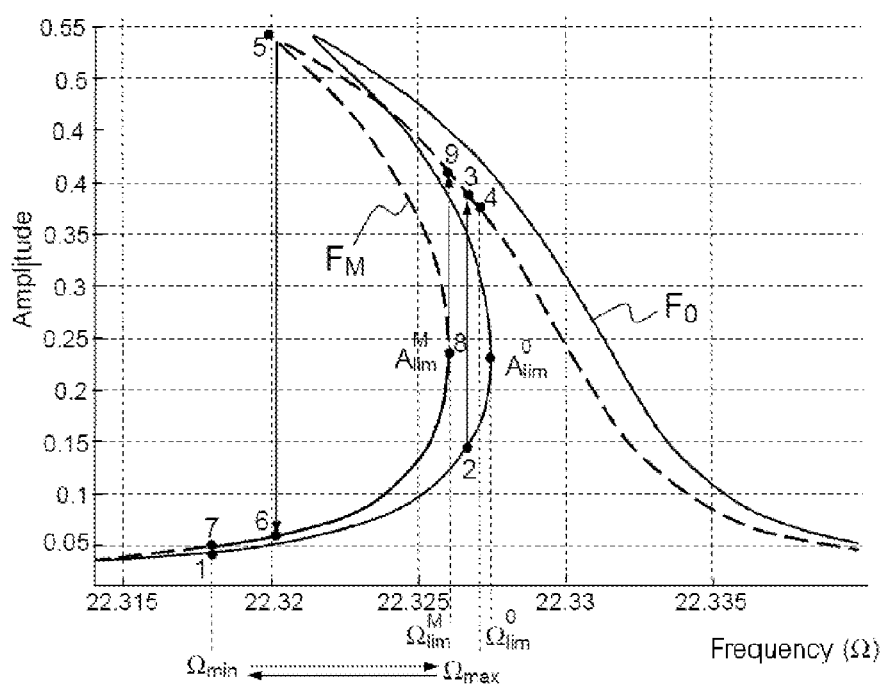

During the detection of a first mass variation, by varying the frequency, the cycles described in FIGS. 6b and 6c are described, following the instant of the event.

More precisely, with the detection of a particle:

In the first case, illustrated in FIG. 6b, where the particle falls at an instant (point 2) such that the scan frequency is situated before $\Omega_{lim}^M$: the hysteresis cycle is then traversed along the paths linked by the succession of the following points: 1-2-3/4-5-6-7-8-9/4-5-6-7-8-9/..., one observes a large amplitude jump from 4 to 5 in a cyclic manner.

In the second case, illustrated by FIG. 6c, where the particle falls at an instant (point 2) such that the scan frequency is situated between $\Omega_{lim}^M$ and $\Omega_{lim}^0$: the hysteresis cycle is then traversed along the paths linked by the succession of the following points: 1-2-3/4-5-6-7-8-9/4-5-6-7-8-9/..., one observes a large amplitude jump from 2 to 3 just once and then from 8 to 9 in a cyclic manner.

In the case of a desorption of the molecule detected at the level of the resonator (for example for a gas particle with low binding energy), corresponding to the return to an initial state, it is desired to be able to reposition the situation in a state situated between the points $A_1$ and $A_2$ belonging to curve $F_0$.

Figure 7A:
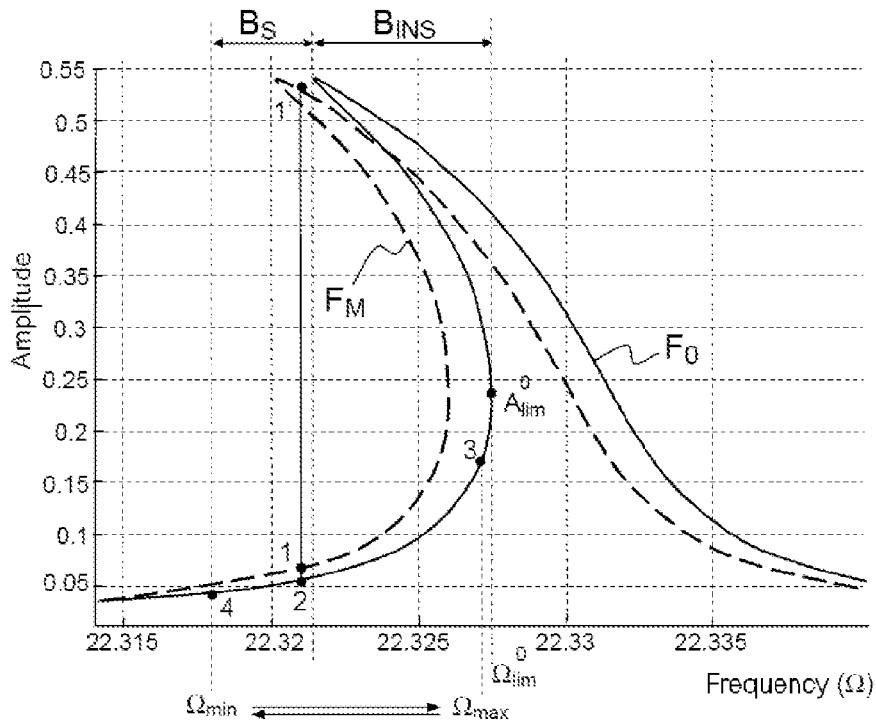
FIGS. 7a and 7b illustrate the cycles used in a device according to the invention, respectively at different instants corresponding to the desorption phenomenon.
Figure 7B:
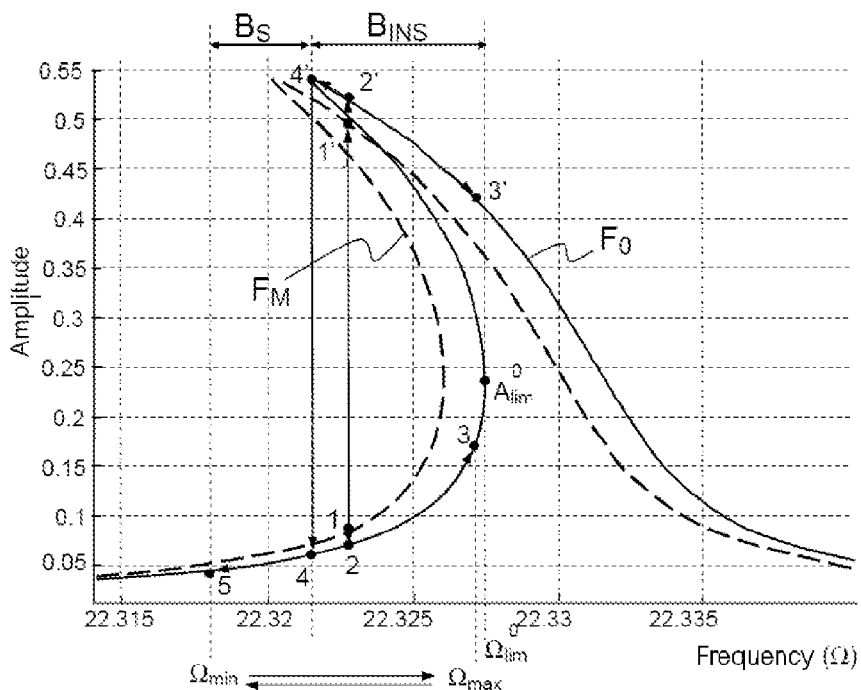

During the desorption of the particle, by varying the frequency, the cycles described in FIGS. 7a and 7b are described, following the instant of the event.

In the first case, illustrated in FIG. 7a, where the particle detaches at an instant (point 2) such that the scan frequency is situated in the span of stable frequencies $B_S$ (a single possible stable amplitude for one and the same frequency): one starts from the point 1 or 1' depending on whether one is situated at the top or at the bottom of the curve $F_M$ and the cycle is then traversed along the paths linked by the succession of the following points: 1 or 1'-2-3/4-3/4-3/...After a jump to the point 2 just once, the curve $F_0$ is traversed between the points 3 and 4, there is no hysteresis cycle nor any associated amplitude jump.

In the second case, illustrated by FIG. 7b, where the particle detaches at an instant (point 2) such that the scan frequency is situated in the span of unstable frequencies $B_{INS}$ (two possible stable amplitudes for one and the same frequency): one starts from the point 1 or 1' depending on whether one is situated at the top or at the bottom of the curve $F_M$ and one jumps either to the point 2 at the bottom of the curve $F_0$ or to the point 2' at the top of the curve $F_0$. If one jumps to the point 2, the cycle is then traversed along the paths linked by the succession of the following points: 1 or 1'-2-3/3-5/3-5/...After a jump to the point 2 just once, the curve $F_0$ is traversed between the points 3 and 5, there is no hysteresis cycle nor any associated amplitude jump. If one jumps to the point 2', the cycle is then traversed along the paths linked by the succession of the following points: 1 or 1'-2'-3'-4'-4-5/3-5/3-5/...After a jump to the point 2' and a jump to the point 4 just once, the curve $F_0$ is traversed between the points 3 and 5, there is no hysteresis cycle nor any associated amplitude jump.

In the case where the mass sensor does not desorb, the detected particles remaining present, it is possible advantageously to continue the interrogation process according to the present invention. Indeed, FIG. 5 highlights a dashed third curve $F_M'$, corresponding to the curve obtained during a second measurement, the curve $F_M$ becoming the new reference curve.

Figure 8:
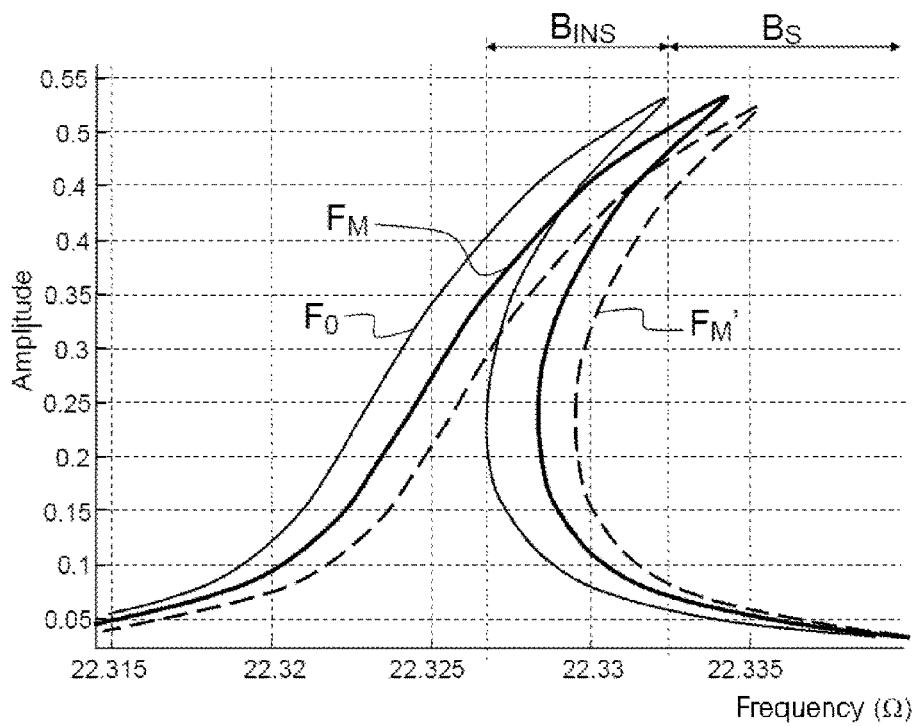
FIG. 8 illustrates another example of response curves generated by the excitation source used in the device of the invention making it possible to integrate a process for reinitializing the measurement, within the framework of a so-called stiffening resonator.

FIG. 8 shows the same type of frequency scan, used in the present invention, within the framework of a stiffening resonator, with resonance frequencies which vary in an increasing manner, during the detection of a perturbation.

Advantageously, the actuation frequency varying in the frequency range $[\Omega_{min}; \Omega_{max}]$ can vary periodically around a predetermined central frequency $\Omega_{op}$, the frequencies $\Omega_{min}$ and $\Omega_{max}$ being adjusted as in the description of FIG. 5.

It is thus considered that the frequency varies according to the following equation:

$$\Omega(t)=\Omega_{op}+\delta\Omega\,\text{Cos}(\varepsilon\pi t+\varphi)$$

with $\varepsilon$ such that $0<\varepsilon\pi/\Omega_{op}<10^{-1}$ with $\varepsilon$ the frequency scan rate.

The excitation frequency is thus modulated in a harmonic manner around a frequency value $\Omega_{op}$ with a modulation amplitude $\delta\Omega$, in the frequency range $[\Omega_{min}; \Omega_{max}]$.

It is of course possible to vary this frequency according to any type of law, such as for example a square law, that may be described in the form of an infinite series:

$$\Omega(t) = \Omega_{op} + \delta\Omega \cdot \frac{4}{\pi}\sum_{n=0}^{\infty}\frac{\sin((2n+1)\varepsilon\pi t)}{(2n+1)}.$$

In the case of the resonator before detection of particles, it is possible to define a bifurcation frequency $\Omega_{lim}$.

The latter can be determined experimentally by observing the frequency response of the device. One then chooses a frequency $\Omega_{max}$ slightly lower than this value, which calibrates the smallest mass that it is possible to detect, for example $|\Omega_{min}-\Omega_{max}|$ lying between 0 and $10^{-1}$ times the frequency $\Omega_{op}$, advantageously $10^{-9}$ and $10^{-1}$ times the frequency $\Omega_{op}$.

One then defines the modulation amplitude $\delta\Omega$ and the value $\Omega_{op}$ with respect to the biggest particle to be detected.

Indeed the minimum frequency $\Omega_{min}=\Omega_{max}-2\ \delta\Omega$ attained by modulation must be situated in a frequency zone where a single vibratory state is possible (quasi-linear).

All the response curves for the beam with or without particle exhibit the same trend (peak deviated towards the low frequencies), shifted all the more to the left the larger the added mass.

Indeed, it may be particularly advantageous to provide for a range of frequencies, such that various types of different mass particles can be detected. Thus within the framework of the detection for example of a set of type of distinct and increasing specific mass particles, there exists a type of particles to be detected having a maximum mass and therefore a specific curve, called the limit curve, maximizing the leftward shift.

Thereafter, the calibration of the scan rates is performed while complying with the following principle: the scan must be fast enough such that during the presence of a particle on the beam, as described in the article by Chaste et al, "A nanomechanical mass sensor with yoctogram resolution", Nature Nanotechnology 2012, at least one complete scan cycle of the modulation interval $[\Omega_{max}-2\ \delta\Omega, \Omega_{max}]$ can be carried out.

This scan frequency $\varepsilon$ can lie between for example 1 Hz and 100 kHz or adjusted such that $0<\varepsilon\pi/\Omega_{op}<10^{-1}$. The principle of frequency modulation is known in the field of RF devices, and can be implanted by many commercial RF voltage sources, and is also used as detection principle for detecting the mechanical motion of an NEMS as described in the article by V. Gouttenoire, T. Barois, S. Perisanu, J.-L. Leclercq, S. T. Purcell, P. Vincent, and A. Ayari, "Digital and FM demodulation of a doubly clamped single-walled carbon-nanotube oscillator: towards a nanotube cell phone," Small (Weinheim an der Bergstrasse, Germany), vol. 6, no. 9, pp. 1060-5, May 2010.

It is thus possible to carry out the transduction of the mechanical motion of the device at the same time as applying the detection principle.

In the course of continuous measurements, and with a state of the resonator which does not revert to its initial state, the perturbations accumulating, a curve $F_M$ becomes an initial curve for the following measurement curve $F_M'$ and so on. In typical cases of this type, it may be beneficial to verify that the new curve of initial state $F_M$ makes it possible to maintain the conditions required at the level of the frequency bounds in the present invention, namely, that one of these bounds belongs to the unstable frequency band and the other to the stable frequency band, making it possible if appropriate to adjust the central frequency $\Omega_{op}$.

To ensure this control, the means for detecting and analysing the signal arising from the electrical detection transducer can advantageously be correlated with the excitation source in a servocontrol loop, when it is detected that the frequency $\Omega_{min}$ is no longer low enough and no longer makes it possible to jump from the higher branch to the lower branch (see points 7 to 8 of FIG. 6b), the frequencies $\Omega_{min}$ and $\Omega_{max}$ determining the thresholds of the largest and of the smallest mass to be detected.

Figure 9:
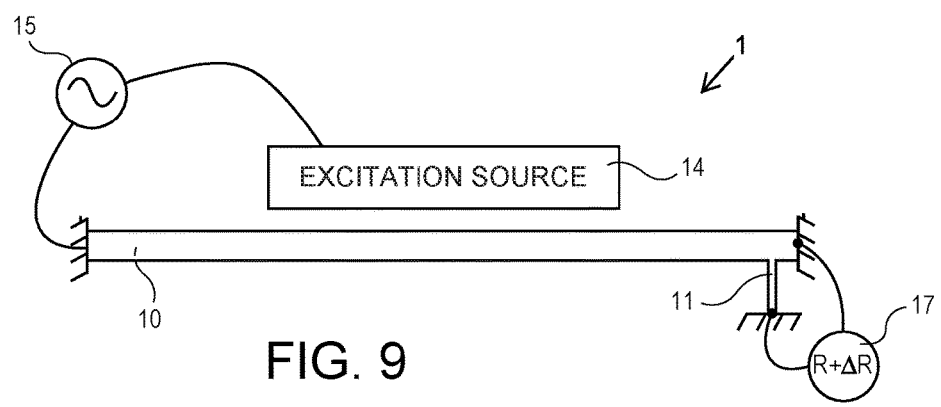
FIG. 9 illustrates an exemplary device for detecting a perturbation.

FIG. 9 shows a device 1 for detecting a perturbation with respect to an initial state. The device 1 may include at least one resonant mechanical element 10 exhibiting a physical parameter sensitive to a perturbation such that the perturbation modifies the resonance frequency of the resonant mechanical element 10. The device 1 may also include an excitation source 14 of the resonant mechanical element making it possible to cause the resonant mechanical element to vibrate in a domain of non-linear amplitude response at a vibration frequency $\Omega$, the amplitude and the frequency being linked by an initial function $f_0(\Omega)$, the perturbation generating a measurement function $f_M(\Omega)$. The device 1 may further include detecting and analyzing means 11 for the variations of amplitude of vibrations of the mechanical element 10 between an amplitude of the function $f_0(\Omega)$, and an amplitude of the function $f_M(\Omega)$. The excitation source 14 may include a piezoelectric, thermoelastic, magnetic, electrostatic, or optical means. The detecting and analyzing means 11 may include at least one of transducer, piezoresistive, capacitive, piezoelectric, optical, and magnetic types.

The invention being generic, it can be applied to a large number of devices, using for example silicon NEMS such as described in the article E. Mile, G. Jourdan, I. Bargatin, S. Labarthe, C. Marcoux, P. Andreucci, S. Hentz, C. Kharrat, E. Colinet, and L. Duraffourg, "In-plane nanoelectromechanical resonators based on silicon nanowire piezoresistive detection," Nanotechnology, vol. 21, no. 16, p. 165504, April 2010, or in the patent application filed by the Applicant: PCT/EP2011/065682.

The invention claimed is:

1. A method for detecting a perturbation of a device comprising resonant mechanical element exhibiting a physical parameter sensitive to the perturbation, said method comprising:
    exciting the resonant mechanical element to vibrate the resonant mechanical element at a non-linear amplitude and at a vibration frequency, the amplitude and the frequency being linked by an initial function, the perturbation generating a measurement function; and
    detecting and analyzing variations of the amplitude between an amplitude of the initial function and an amplitude of the measurement function; and
    wherein the initial function exhibits a bifurcation frequency, corresponding to a change of the frequency as a function of amplitude and possessing at least one unstable frequency band having at least two stable amplitudes for the same frequency, and at least one stable frequency band having a single stable amplitude corresponding to a single frequency,
    wherein the exciting is carried out at a variable vibration frequency within a frequency band defined by a minimum frequency and a maximum frequency, and according to at least one frequency cycle centered on a central frequency $\Omega_{op}$, and one of the minimum and maximum frequencies being situated in the stable frequency band of the initial function, the other maximum or minimum frequency being situated in the unstable frequency band.

2. The method of claim 1, wherein the vibration frequency varies around the central frequency $\Omega_{op}$ according to $\Omega(t)=\Omega_{op}+\delta\Omega\ \text{Cos}(\varepsilon\pi t+\varphi)$, with $\varepsilon$ the frequency scan rate, $\varphi$ having a value lying between 0 and $2\pi$.

3. The method of claim 1, wherein a frequency scan rate $\varepsilon$ of a cycle lies between about 1 Hz and 100 kHz, or with a ratio $\varepsilon\pi/\Omega_{op}$ such that $0<\varepsilon\pi/\Omega_{op}<10^{-1}$.

4. A device for detecting a perturbation with respect to an initial state, comprising:
- resonant mechanical element exhibiting a physical parameter sensitive to a perturbation such that the perturbation modifies a resonance frequency of said resonant mechanical element;
- an excitation source configured to cause the resonant mechanical element to vibrate at a non-linear amplitude and at a vibration frequency, the amplitude and the frequency being linked by an initial function, the perturbation generating a measurement function; and
- means for detecting variations of amplitude of vibrations of the mechanical element between an amplitude of the initial function, and an amplitude of the measurement function,
- wherein the initial function, exhibits a bifurcation frequency corresponding to an increase or a decrease of the frequency as a function of amplitude and possesses at least one unstable frequency band in which there exist at least two stable amplitudes for one and the same frequency, and at least one stable frequency band in which a single stable amplitude corresponds to a single frequency, and
- wherein the excitation source comprises means which vary the vibration frequency in a frequency band defined by a minimum frequency and a maximum frequency and according to at least one frequency cycle centered on a central frequency, one of the minimum or maximum frequencies being situated in the stable frequency band of the initial function, the other maximum or minimum frequency being situated in the unstable frequency band.

5. The device of claim 4, wherein the resonant mechanical element is a resonator beam and the excitation source comprises an actuation electrode facing the resonator.

6. The device of claim 5, wherein the resonator beam has nanometric dimensions, a drive electrode is configured to apply voltages of the order of a few Volts, a gap between the drive electrode and the resonator being of the order of 10 nm and 1 µm.

7. A mass sensor comprising a device according to claim 4.

8. A mass spectrometer comprising a device according to claim 4, and being configured to measure a mass of particles deposited on the resonant mechanical element.

* * * * *